United States Patent [19]

Leonard

[11] Patent Number: 4,580,979
[45] Date of Patent: Apr. 8, 1986

[54] DRILLING SYSTEMS BY VIBRATIONS
[75] Inventor: Henri Leonard, Besancon, France
[73] Assignee: Micro-Mega S.A., Besancon, France
[21] Appl. No.: 683,876
[22] Filed: Dec. 20, 1984
[30] Foreign Application Priority Data
Dec. 20, 1983 [FR] France .................. 83 20527
[51] Int. Cl.⁴ .............................................. A61C 1/14
[52] U.S. Cl. .................................. 433/127; 433/118; 433/147
[58] Field of Search .............. 433/126, 118, 119, 147, 433/144, 127, 128; 279/99, 100, 101, 1 F, 8

[56] References Cited
U.S. PATENT DOCUMENTS

| 3,471,929 | 10/1969 | Boone | 433/144 |
| 3,892,040 | 7/1975 | Marquis | 132/89 |
| 3,924,334 | 12/1975 | Lentine et al. | 433/147 |
| 4,484,891 | 11/1984 | Nash | 433/128 |

FOREIGN PATENT DOCUMENTS 3337367  5/1984  Fed. Rep. of Germany ...... 433/118

Primary Examiner—John J. Wilson
Attorney, Agent, or Firm—Robert E. Burns; Emmanuel J. Lobato; Bruce L. Adams

[57] ABSTRACT

A system for maintaining in the head of a vibratable dental tool holder a dental tool releasably held axially in fixed position in a transverse passage oblique to the longitudinal axis of the dental tool holder. The system comprises a first sleeve axially of the dental tool holder having a leading edge bearing against the dental tool. A second sleeve is threaded on the dental tool holder and it keeps the first sleeve in close contact with the dental tool keeping it from moving axially away from the dental tool in response to vibration of the dental tool holder during operation.

4 Claims, 1 Drawing Figure

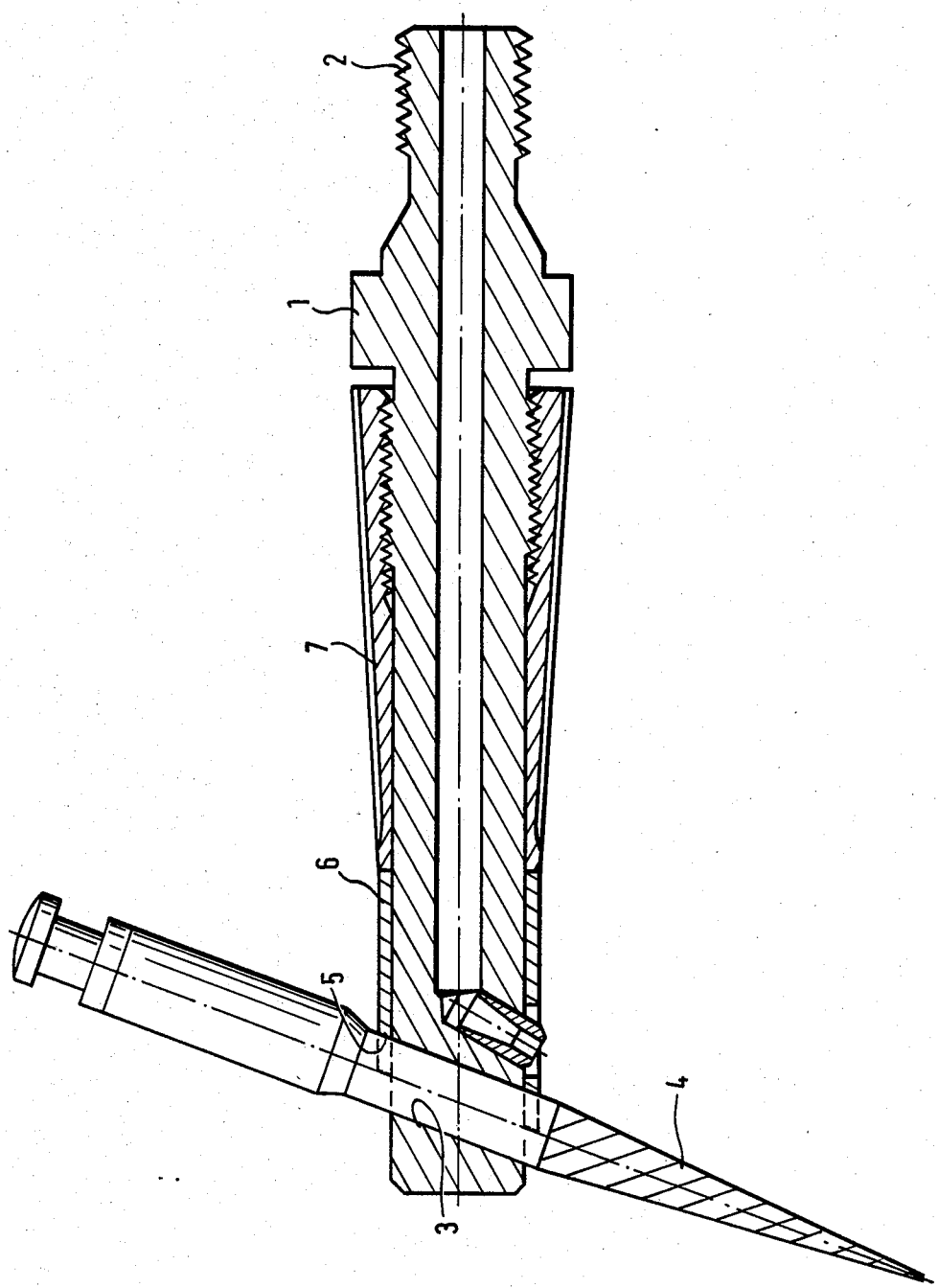

DRILLING SYSTEMS BY VIBRATIONS

BACKGROUND OF THE INVENTION

The present invention concerns a drilling systems operable by vibrations.

In this kind of system, a tool such as the driller of the type described notably in the French Pat. No. 82/18545, is inserted into a housing set obliquely in relation to the axis of the tool-holder, itself equipped with a device generating vibrations, for instance a pneumatic turbine, whereof the rotor comprises an unbalance and whereof the rotation at very high speed generates vibrations of about the frequency 300 HZ.

A device known for fastening the tool, particularly a drill, in its housing consists of a socket co-axial to the tool-holder, and that, by screwing towards above the external form of the said tool-holder, till the contact of the drill determines the blocking of the same.

This device shows a disadvantage that is inherent in the system itself. Namely, by functionning of this system through vibrations, these ones cause inevitably the unscrewing of this socket and therefore the unclamping of the driller that, even if not freed from its housing, receives no longer the vibrations achieving its efficiency.

SUMMARY OF THE INVENTION

The present invention is directed to remedy this disadvantage. It consists in securing the blocking of the tool in its housing through a first element that is forcibly driven on to the conical seat of the tool-holder, this first element being itself kept in the place by a socket similar to the socket of the known system. Thus it is obtained an effect of counter-nut or lock nut of the second element upon the first, securing its immobility and therefore the locking of the drill in place, in spite of vibrations to which it is submitted.

The fit of the first element on the tool-holder can simply be made by means of friction upon its seat, but preferably it is made by screwing, even in the same direction as the socket, in the same way as the real assemblage nut/counter-nut.

BRIEF DESCRIPTION OF THE DRAWING

The invention is better understood by the attached drawing, whereof the single FIGURE, is a sectional view along the axial symmetry plane of the system according to the invention.

DESCRIPTION OF THE PREFERRED EMBODIMENT

On this drawing are shown the tool-holder 1 comprising on its posterior portion the mechanism 2 generating vibrations, as type already known in itself, for instance a pneumatic turbine with unbalance In the housing passage 3 of the head of this tool-holder is inserted the tool 4, such as a drill that is oblique in relation to the axis of the tool-holder. According to the invention, this drill is blocked or locked in its position through the upper edge 5 of a first element of fastening 6, consisting of a threaded cone sleeve screwed on the fore part of the tool-holder, this first element being itself immobilized by screwing on its rear part through a second element or sleeve 7, equally screwed on the tool-holder in the same way as the single socket of the principal patent.

The sleeve socket 7 blocks the element 6 precluding its unscrewing in the same way as happens to a lock nut against a lock nut. Nut 2T prevents the element 6 from moving axially away from the drill 4 by uncoupling it from the vibrating tool-holder 1; here is the aim of this invention.

Of course the first element 6 could be conical as well as cylindrical, fitted through friction or screwing on the head of the tool-holder.

I claim:

1. In combination a vibratable tool holder having a head for holding a dental tool, said head having a through transverse passage through which the tool extends, a tool extending transversely of a longitudinal axis of the tool holder, fastening means for holding the tool axially in position on the tool holder comprising, a first sleeve extending axially on the tool holder and having a leading edge bearing against the tool clamping it against said edge and a side of said passage, a second sleeve coaxial with the first sleeve threaded on the tool holder and having a leading edge bearing against a trailing edge of the first sleeve to maintain the first sleeve from axial movement on the tool holder due to vibration thereof.

2. System for fastening a dentristry tool in a head of an elongated tool holder vibratable in use, the head having a transverse passage oblique to the longitudinal axis of the tool holder, an elongated tool extending through said passage, said system consisting of a first sleeve extending axially on the tool holder in a direction away from the head of the tool holder and having an edge shaped to extend partly around the tool and bear thereagainst, and a second sleeve coaxial with the first sleeve threaded on the tool holder holding the first sleeve from axial movement away from the tool, whereby the tool is held fixed on the tool holder when it is vibrated.

3. System according to claim 2, in which the second sleeve is conical and extends axially on the tool holder and bears against the first sleeve.

4. System according to claim 2, in which said second sleeve extends axially on the tool holder an axial extent greater than the axial extent of the first sleeve and is threaded only along a limited axial extent of its axial length.

* * * * *